United States Patent [19]

Taylor et al.

[11] Patent Number: 4,831,146

[45] Date of Patent: May 16, 1989

[54] PROCESS FOR PREPARING TRIACETONE AMINE AND OTHER OXOPIPERIDINES

[75] Inventors: Denise B. Taylor, Waterford, Conn.; Barton Milligan, Coplay, Pa.

[73] Assignee: Air Products and Chemicals, Inc., Allentown, Pa.

[21] Appl. No.: 170,505

[22] Filed: Mar. 21, 1988

[51] Int. Cl.$^4$ .......................................... C07D 211/74
[52] U.S. Cl. .................................................. 546/242
[58] Field of Search ........................................ 546/242

[56] References Cited

U.S. PATENT DOCUMENTS

| | | |
|---|---|---|
| 3,904,625 | 9/1975 | Oudealink ............................ 544/231 |
| 3,943,139 | 3/1976 | Orban et al. ........................ 546/242 |
| 3,959,295 | 5/1976 | Orban et al. ........................ 546/242 |
| 3,959,298 | 5/1976 | Murayamai et al. ................ 546/242 |
| 4,275,211 | 6/1981 | Orban et al. ........................ 546/242 |
| 4,356,308 | 10/1982 | Wiezer et al. ...................... 546/242 |

*Primary Examiner*—Richard A. Schwartz
*Attorney, Agent, or Firm*—Russell L. Brewer; James C. Simmons; William F. Marsh

[57] ABSTRACT

This invention relates to an improved catalytic process for producing 2,2,6,6-tetraalkyl-4-oxopiperidines by the reaction of a ketone and ammonia. The improvement resides in using a catalytic amount of a super acid, i.e., a perfluorinated sulfonic acid polymer or perfluorinated alkyl sulfonic acid as the catalyst.

10 Claims, No Drawings

PROCESS FOR PREPARING TRIACETONE AMINE AND OTHER OXOPIPERIDINES

TECHNICAL FIELD

This invention relates to a process for preparing 2,2,6,6-tetraalkyl-4-oxopiperidines and particularly a 2,2,6,6-tetramethyl-4-oxopiperidine commonly referred to a triacetone amine. These compositions are widely used as stabilizers for synthetic high molecular weight polymers and particularly, stabilizers against ultra violet light and heat induced discoloration.

BACKGROUND OF THE INVENTION

Several patents describe the 2,2,6,6-tetraalkyl-4-oxopiperidines and their synthesis and the following patents are representative:

U.S. Pat. No. 3,959,295 discloses the preparation of triacetone amine by reacting acetone and ammonia in the presence of an acidic catalyst, i.e., Lewis acids, protonic acids, and their salts with ammonia or with organic bases such as boron trifluoride, ammonium chloride or sulfuric acid. The process comprises two steps i.e., the first wherein ammonia is reacted with ammonia in the presence of an acid catalyst in an amount from 0.2 to 12 mole % relative to the acetone at a temperature of from 5° to 60° C. and the second, completing the reaction with or without the addition of acetone but using a total amount of acetone of 1.6 moles or greater per mole of ammonia.

U.S. Pat. No. 4,275,211 discloses a process of producing tetraalkyl-4-oxopiperidines such as triacetone amine by effecting reaction between acetone and ammonia at temperatures from 25°–55° C. in the presence of a strongly acid ion exchanger having a medium or large mesh size or having large macropores. These strongly acidic cations exchangers are based mainly on styrene with divinylbenzene as a crosslinking agent and then sulfonated. Lewatit SC 104/H resin is an example of such a strong acid cation exchanger. It was acknowledged that ion exchange catalysts had been used in the past (U.S. Pat. No. 3,904,625) but such processses were of little success.

U.S. Pat. No. 3,943,139 discloses a process for producing triacetone amine by reacting phorone and ammonia under pressures from 1–3 bars and temperatures from 60°–110° C.

U.S. Pat. No. 3,959,298 discloses a process for preparing triacetone amine by reacting acetonine with water in the presence of an acid catalyst present in an amount to provide at least 12.5 mole % based on the acetonine. Examples of acid catalysts include carboxylic acids, mineral acids, organic sulfur-oxygen acids or organic phosphorus-oxygen acids. Specific examples include saturated and unsaturated monobasic aliphatic acids such as acetic acid; methylsulfuric acid and sulfonic acids such as methane sulfonic acids, benzene sulfonic acids and the phosphorus acids such as diethyl-phosphonic acid or benzene phosphinic acid.

U.S. Pat. No. 3,904,625 discloses a process for preparing 2,3,4,5-tetrahydropyrimidines (THP) by reacting a carbonyl compound such as a ketone or aldehyde with ammonia in the presence of a ion exchange catalyst preferably an anionic resin such as a sulfonated resin commonly sold under the trademark AMBERLITE ®. Temperatures of reaction range from 0° to 100° C. preferably from 10° to 40° C. with reaction times ranging from 1 to 3 hours typically.

SUMMARY OF THE INVENTION

This invention pertains to a process for the synthesis of 2,2,6,6-tetraalkyl-4-oxopiperidines such as triacetone amine from acetone and ammonia in the presence an acidic catalyst. More specifically, the process involves effecting the reaction between a ketone and ammonia in the presence of a perfluorinated polymer containing pendent sulfonic acid groups or perfluorinated alkyl sulfonic acid.

Several advantages are achieved utilizing the catalyst system described. These include:

the ability to carry out the process in one step with conversion of ketone to oxopiperidine rather than through a two-step process;

the ability to easily separate the catalyst systems from the reaction medium; and the ability to achieve excellent conversion of ketone to oxopiperidine at reasonable reaction rates through enhanced catalysis.

DETAILED DESCRIPTION OF THE INVENTION

This invention relates to the improvement in a process for preparing 2,2,6,6-tetraalkyl-4-oxopiperidines which are represented by formula:

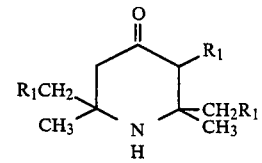

from a ketone of the formula $R_1$—$CH_2$—$C(O)$—$CH_3$ wherein $R_1$ is hydrogen or a $C_1$-$C_4$ alkyl group and ammonia. The reaction between the ketone and ammonia is carried in the process of catalyst system which consists of a perfluorinated polymer having pendent sulfonic acid groups or a perfluorinated alkyl sulfonic acid. A common form of perfluorinated polymer having sulfonic acid groups is sold under the trademark NAFION ®. Another acid is trifluoroalkyl sulfonic acid such as triflic acid (trifluoromethane sulfonic acid).

Ketones which are used for reaction with ammonia to produce the tetraalkyl-4-oxopiperidines, particularly, triacetone amine, include n-butyl-methylketone, acetone, n-propylmethylketone, ethylmethyl ketone or mixtures of ketones. It is also possible to use condensation products of the ketones, such as diacetone alcohol, phorone or acid condensation products of acetone and ammonia such as diacetone amine, triacetone diamine or acetonine. Each of these are equivalents of the ketones used for reaction or are intermediate reaction products of the ketone and tetraalkyloxopiperidine. For purposes herein such compositions are included within the term ketone.

The perfluorinated polymer having pendent sulfonic acid groups in the structure and useful in the process are known. Typically, the amount of acid groups will range from about 0.01 to 15 milliequivalents acid per gram of catalyst and preferably from about 0.1 to 10 milliequivalents acid per gram of catalyst.

A preferred polymer used as the catalyst contains a repeating structure represented by the formula

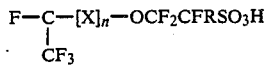

or

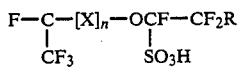

where n is 0, 1 or 2; R is fluorine or a perfluoro alkyl radical having from 1 to 10 carbon atoms and X is represented by a group consisting of $[O(CF_3)_m]$, $[OCF_2CFY]$, or $[OCFYCF_2]$ where n is an integer from 2 to 10, and Y is fluorine or a trifluoromethyl radical.

Other perfluorinated polymer catalysts containing sulfonic acid groups are described in U.S. Pat. Nos. 3,282,875; 3,882,093; 4,022,847; 4,060,565 and 4,446,329 which are incorporated by reference. Polymer catalysts of the above-noted structure can be prepared in various ways. One method, disclosed in Connolly, et al., U.S. Pat. No. 3,282,875 and Cavanaugh, et al., U.S. Pat. No. 3,882,093, and incorporated by reference comprises polymerizing vinyl compounds of the formula:

or

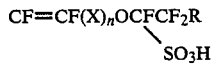

It is also possible to prepare catalysts for the present invention by copolymerizing vinyl ethers with perfluoroethylene and/or perfluoro-alpha-olefins. A preferred copolymer prepared by polymerizing perfluoroethylene with a perfluorovinyl ether containing attached sulfonic acid groups would have the following structure:

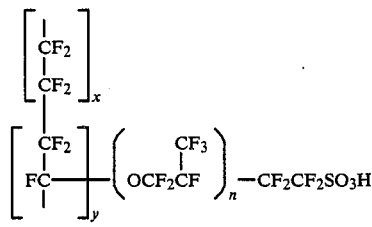

wherein n=1 or 2 and the ratio of x over y varies from about 2 to about 50. The polymer is available commercially under the trademark NAFION. Catalysts of the above-noted structure offer the advantages of high concentrations of accessible acid groups in a solid phase.

The catalysts of the present invention also may be utilized in a supported or unsupported medium, however, supported catalysts are preferred. Typically, the catalyst is supported on a porous inert solid having a pore diameter of between 50 and 600 Angstroms or higher and typically are inorganic oxides such as alumina, fluorided alumina, zirconia, silica, silica-alumina, bauxite, kieselguhr, kaolin, charcoal, porous glass, etc.

The reaction of ammonia with the ketone is performed at a temperature of from about 0° to 100° C. but preferred temperatures range from 40°-75° C. Pressures range from about atmospheric pressure to 1000 psi preferably less than 100 psig. Reaction times range from about 10 to 100 hours. The mole ratio of ketone to ammonia ranges from about 2 to 15:1 and preferably 0.4 to 8 moles ketone per mole of ammonia. The reaction can be carried out in a batch or a fixed bed with catalyst loadings in a batch reactor ranging from about 1 to 30% by weight of ketone. The batch process is usually preferred.

The following examples are intended to represent various embodiments of the invention and are not intended to restrict the scope thereof.

EXAMPLE 1

Triacetoneamine Synthesis Using NAFION ® Resin

Several runs were carried out in a conventional stirred reactor having 50 mls of volume and a sample port. The procedure involved adding a preselected amount of fluorinated polymer containing sulfonic acid groups and sold under the trademark NAFION 50 ® by DuPont as well as a preselected amount of acetone. After the addition of acetone and catalyst was made to the reactor, the reactor was closed and ammonia was added in a preselected amount. The contents were heated to 50° C. and samples taken. Table 1 sets forth the run sequence and data regarding reaction conditions and results.

TABLE 1

| Run | Acetone gms | NH3 qm | Nafion ® powder gms | N/R | Pressure psig | Reaction Time/Hr | Triacetone Amine wt % | Acetone wt % | Acetonine wt % |
|---|---|---|---|---|---|---|---|---|---|
| 1 | 19.76 | 0.993 | 1.873 | 5.6/1 | 10 | 70 | 31.1 | 44.4 | — |
| 2 | 19.63 | 0.934 | 1.779 | 6.15/1 | 10 | 49.5 | 23.1 | 56.4 | — |
| 3 | 20.06 | 1.126 | 4.93 | 5.2/1 | 10 | 25 | 28.1 | 34.6 | — |
| 4 | 20.04 | 1.163 | 5.08 | 5.0/1 | 10 | 70 | 30.7 | 35.7 | — |
| 5 | 20.05 | 1.119 | 5.02 | 5.25 | 10 | 49.5 | 30.7 | 37 | — |
| 6A | 19.81 | 1.312 | 1.79 | 6.4/1 | 10 | 4 | 5.9 | 58.5 | 16.4 |
| B | — | — | — | — | 10 | 8 | 11.5 | 54.6 | 14.3 |
| C | — | — | — | — | 10 | 12 | 14.5 | 47.3 | 12.5 |
| D | — | — | — | — | 10 | 24 | 27.4 | 44.0 | 6.8 |
| E | — | — | — | — | 10 | 54 | 34.4 | 33.7 | 2.4 |
| 7A | 20.05 | 1.145 | 5.01 | 5.1/1 | 10 | 12 | 23.6 | 36.7 | — |
| B | — | — | — | — | 10 | 25.5 | 33.4 | 36.3 | — |
| C | — | — | — | — | 10 | 29.8 | 30.7 | 32.8 | — |
| D | — | — | — | — | 10 | 10 | 30 | 33.02 | 35.9 |

The above results show excellent conversion of acetone to triacetone amine within a reasonable reaction time. Runs 6 & 7 show an excellent reaction rate is achieved with the Nafion ® Catalyst as the reaction proceeds toward completion.

EXAMPLE 2

Triacetone Amine Variable Temperature

Acetone (118.77 g, 2.05 mol) and NAFION ® resin (5.59 g) were added to a 250 mL Ehrlenmeyer flash, NH$_3$ (4.0 g, 0.24 mol) was bubbled in. The flask was covered with PARAFILM ® sheet and allowed to stir at room temperature (19° C.). At 25 h, additional NH$_3$ (2.6 g, 0.15 mol) was added. At 45 h, additional NAFION ® resin (5.6 g) was added and the reaction allowed to stir. At 69 h the reaction temperature was raised to 50° C.

| Time Hours | Acetone Consumed | Amount of Consumed Acetone Converted to Triacetoneamine | Total Conversion To TAA |
|---|---|---|---|
| 25 h | 31.61% | 6.45% | 2.04% |
| 45 h | 47.91% | 8.30% | 3.98% |
| 69 h | 49.70% | 16.09% | 8.00% |
| 76 h | 50.67% | 27.46% | 13.91% |
| 118 h | 60.74% | 75.34% | 45.76% |

Excellent yields can be obtained at reasonable rates at the higher temperature. The reaction rate was much slower at lower temperatures.

EXAMPLE 3

Triacetoneamine Using Ammonia

Acetone (200 g, 3.45 mol) was added to a 500 mL Morton flask fitted with a mechanical stirrer. NH$_3$(g) was bubbled in for 45 minutes. NAFION ® resin (22.8 g) was added. The reaction was stirred at 50° C. Samples were taken every hour for the first 8 h of the reaction, and again at 25 h.

| Time | Acetone Consumed | Amount of Consumed Acetone Converted to Triacetoneamine | AOCA CTA* | Total Conversion to TAA | TC TA** |
|---|---|---|---|---|---|
| 0 h | 7.22% | 0.89% | 96.08% | 0.06% | 6.94% |
| 1 h | 14.78% | 10.96% | 87.03% | 1.62% | 12.86% |
| 2 h | 15.01% | 36.68% | 43.11% | 5.51% | 6.47% |
| 3 h | 17.37% | 58.10% | 19.24% | 10.09% | 3.34% |
| 4 h | 19.15% | 66.55% | 13.62% | 12.74% | 2.61% |
| 5 h | 21.22% | 74.03% | 7.71% | 15.71% | 1.64% |
| 6 h | 22.21% | 76.52% | 6.18% | 17.00% | 1.37% |
| 7 h | 23.18% | 79.13% | 4.71% | 18.34% | 1.09% |
| 8 h | 23.78% | 80.98% | 3.69% | 19.26% | 0.87% |
| 25 h | 29.01% | 84.99% | 0.00% | 24.66% | 0.00% |

*Amount of Consumed Acetone Converted to Acetonin
**Total Conversion to Acetonin

EXAMPLE 4

Triacetone Amine Using Ammonium Hydroxide

Acetone (200 g, 3.45 mol) and concentrated ammonium hydroxide (31 mL, 0.46 mol NH$_3$) were added to a Morton flask fitted with a mechanical stirrer and containing NAFION ® resin (26.57 g). The reaction was stirred at 50° C.

| Time | Acetone Consumed | Amount of Consumed Acetone Converted to Triacetoneamine | AOCA CTA* | Total Conversion to TAA | TC TA** |
|---|---|---|---|---|---|
| 0 h | 14.18% | 0.00% | 100.00% | 0.00% | 14.18% |
| 1 h | 15.90% | 1.45% | 92.57% | 0.23% | 14.72% |
| 2 h | 24.91% | 31.71% | 34.00% | 7.90% | 8.47% |
| 3 h | 28.09% | 44.01% | 22.86% | 12.36% | 6.42% |
| 4 h | 30.12% | 49.73% | 20.26% | 14.98% | 6.10% |
| 5 h | 31.83% | 56.18% | 14.09% | 17.88% | 4.48% |
| 6 h | 32.86% | 58.57% | 11.50% | 19.25% | 3.78% |
| 7 h | 30.37% | 63.06% | 8.27% | 19.15% | 2.51% |
| 8 h | 34.63% | 65.34% | 7.44% | 22.63% | 2.58% |
| 9 h | 36.24% | 67.48% | 5.81% | 24.45% | 1.87% |

*Amount of Consumed Acetone Converted to Acetonin
**Total Conversion to Acetonin Example 4 shows that ammonium hydroxide can be used in place of ammonia. Again, excellent conversions of acetone to triacetoneamine were achieved.

EXAMPLE 5

Triacetone Amine with Triflic Acid

Acetone (118.5 g, 2.04 mol), NH$_3$ (5.6 g, 0.33 mol) and trifluoromethane sulfonic acid (1.21 g, 0 008 mol) were combined in a 300 ml autoclave. The reaction was stirred at 50° C. at autogenous pressure (10 psig).

| Time | Acetone Consumed | Amount of Consumed Acetone Converted to Triacetoneamine | Total Conversion To TAA |
|---|---|---|---|
| 3 h | 18.80% | 15.04% | 2.83% |
| 24 h | 36.96% | 74.33% | 27.47% |
| 28 h | 37.91% | 75.41% | 28.59% |

Excellent yields were obtained with this catalyst thus showing extended activity because of the pendent fluorine groups.

EXAMPLE 6

Comparative Example Using
NAFION ®, AMBERLYST ® and IRC-50 ® Catalysts

A series of reactions were carried out between acetone and ammonia by charging 3.45 moles of acetone and 15 mls of 10–35 mesh NAFION ® powder in the hydrogen ion form to a 250 ml Ehrlenmeyer flask. Then, 0.46 moles ammonia as 31 ml ammonium/hydroxide were added and the contents heated to 50° C. with stirring. Samples were taken over a period ranging from 20 to 75 hours.

The above procedure was repeated except that a conventional ion exchange resin in a hydrogen form sold under the trademark AMBERLYST-15 ® was substituted for the NAFION ® catalyst. AMBERLYST ® is a styrene-divinyl benzene polymer containing pendent sulfonic acid groups and is the type of polymer acid used in U.S. Pat. No. 3,904,625. No fluorine atoms are present in the polymer.

A third run was made using a commercial ion exchange resin in hydrogen form sold under the trademark IRC-50 ®. Approximately 20 mls of catalyst were used. Table 2 represents the results. TAA refers to triacetone amine.

TABLE 2

| Run | Catalyst | Time/Hr. | % Conversion TAA |
|---|---|---|---|
| 1. | Nafion ® | 22.5 | 24.1 |
|  |  | 46.5 | 27.7 |
|  |  | 68.5 | 28.8 |
| 2. | Amberlyst-15 ® | 28 | 4.09 |
|  |  | 70 | 12.24 |
| 3* | IRC-50 ® | 24 | 0 |
|  |  | 55 | 2.5 |

*Run 3, the reaction was terminated at 55 hours since conversion was extremely low as compared to the NAFION ® catalyst system.

From the above results, it is clear that the NAFION ® catalyst system was much more effective than the conventional ion exchange resins even though all were sulfonic acid containing catalyst systems. It is believed the increased activity of the NAFION ® catalyst as compared to the conventional sulfonic acid terminated polymers is due to the presence of fluorine groups. This benefit was also achieved using triflic acid as described in Example 5.

What is claimed is:

1. In a process for producing a tetraalkyl-4-oxopiperidine compound represented by the formula:

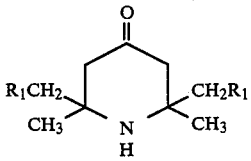

in which $R_1$ is hydrogen or $C_1$-$C_4$ alkyl, from a ketone of the formula $R_1$—$CH_2$—$C(O)$—$CH_3$ wherein $R_1$ has the meaning recited in the formula above and ammonia at temperatures of from 0°–100° C. in the presence of a catalyst, the improvement which comprises using as said catalyst a super acid selected from the group consisting of perfluorinated polymeric resins having sulfonic acid groups pendent therefrom or a perfluorinated alkyl sulfonic acid.

2. The process of claim 1 wherein $R_1$ is hydrogen or $C_1$ methyl.

3. The process of claim 2 wherein said catalyst is a perfluorinated polymer having a repeating structure represented by the formula:

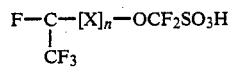

or

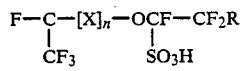

where n is 0, 1 or 2; R is fluorine or a perfluoro alkyl radical having from 1 to 10 carbon atoms and X is represented by a group consisting of $[O(CF_3)_m]$, $[OCF_2CFY]$, or $[OCFYCF_2]$ where m is an integer from 2 to 10, and Y is fluorine or a trifluoromethyl radical.

4. The process of claim 3 wherein in said catalyst X is $OCF_2CFY$, Y is $CF_3$, and n is 2.

5. The process of claim 4 wherein the mol ratio of ketone to ammonia ranges from 2 to 15:1.

6. The process of claim 5 wherein the 0.1 to 10 milliequivalents sulfonic acid are present per mol of ketone.

7. The process of claim 6 wherein $R_1$ is hydrogen.

8. The process of claim 2 wherein said catalyst is triflic acid.

9. The process of claim 8 wherein the catalyst is present in an amount from 1–30% by weight of the ketone.

10. In a process for producing triacetone amine by reacting ammonia with acetone in the presence of an acidic catalyst, the improvement which comprises carrying out said reaction in the presence of a catalyst having a repeating structure represented by the formula:

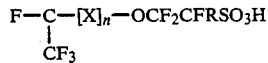

wherein n is 1, 2, or 3 X is $OCF_2CFY$, where Y is trifluoromethyl and R is fluorine.

* * * * *